United States Patent
Zhang et al.

(10) Patent No.: US 7,580,754 B2
(45) Date of Patent: Aug. 25, 2009

(54) IMPLANTABLE ACOUSTIC SENSOR

(75) Inventors: Lei Andy Zhang, East Melbourne (AU); Peter Misha Seligman, East Melbourne (AU); Anthony Klein, Parkville (AU); Robert Cowan, East Melbourne (AU)

(73) Assignee: Cochlear Limited, Lane Cove (AU)

( * ) Notice: Subject to any disclaimer, the term of this patent is extended or adjusted under 35 U.S.C. 154(b) by 5 days.

(21) Appl. No.: 10/986,812

(22) Filed: Nov. 15, 2004

(65) Prior Publication Data
US 2005/0177204 A1    Aug. 11, 2005

(30) Foreign Application Priority Data
Nov. 14, 2003    (AU) .............................. 2003906267

(51) Int. Cl.
*A61N 1/18* (2006.01)
(52) U.S. Cl. ................ 607/55; 607/56; 607/57
(58) Field of Classification Search ............. 607/55–57; 600/25
See application file for complete search history.

(56) References Cited

U.S. PATENT DOCUMENTS

| 5,061,282 | A  |   | 10/1991 | Jacobs |           |
|-----------|----|---|---------|--------|-----------|
| 5,772,575 | A  | * | 6/1998  | Lesinski et al. | 600/25 |
| 5,782,744 | A  | * | 7/1998  | Money  | 600/25    |
| 6,259,951 | B1 | * | 7/2001  | Kuzma et al. | 607/57 |

OTHER PUBLICATIONS

"Product Search—Piezoceramic Mics—BL series." Knowles Electronics. <http://www.knowles.com/search/search.do> (Feb. 25, 2008).*

* cited by examiner

*Primary Examiner*—Carl H Layno
*Assistant Examiner*—Deborah Malamud
(74) *Attorney, Agent, or Firm*—Connolly Bove Lodge & Hutz LLP

(57) ABSTRACT

An acoustic sensor, suitable for use in a totally implanted hearing prosthesis, uses an elongate member and piezoelectric sensor to detect acoustic signals when the sensor is implanted so as to be in fluid communication with the perilymph. The sensor may be applied in systems which are not totally implanted.

52 Claims, 6 Drawing Sheets

IMPLANTABLE ACOUSTIC SENSOR

CROSS-REFERENCE TO RELATED APPLICATIONS

This application claims priority from Australian Provisional Patent Application No. 2003906267 filed on Nov. 14, 2003, the contents of which is incorporated herein by reference.

BACKGROUND

1. Field of the Invention

The present invention relates to an acoustic sensor, and in particular, to an acoustic sensor for use with a hearing prosthesis.

2. Related Art

Implantable hearing prostheses are used to provide therapy to individuals suffering from hearing loss.

Hearing prostheses, such as conventional hearing aids and more recently cochlear implants, have traditionally been required to perform two distinct functions, namely the detection and processing of ambient sound into a processed signal, and the use of the processed signal to generate a stimulus for delivery to the auditory system.

In implantable systems such as cochlear implants and implantable hearing aids, these functions are typically performed by separate parts of the systems. The detection and processing of speech and ambient sound typically occurs in the external part and includes a microphone for sensing the speech and ambient sounds and a processing unit for processing the speech and ambient sounds into a signal to be transmitted to the implanted section. The delivery of the processed signal to the auditory system typically occurs in the internal or implanted part of the system, whereby the processed signal is received by an implanted stimulator unit which decodes the processed signal and delivers the appropriate stimulation, via intracochlear electrodes or electromechanical stimulation, to the auditory pathway to provide the recipient with a perception of the speech and ambient sounds.

As a result, a common aspect of conventional hearing prostheses has been the need for the recipient to carry or wear the external part of the system in a manner which ensures that there is constant communication between the external part and the implanted part. The constant presence of the external part of the system can greatly restrict the type of activities the recipient can perform whilst using the prosthesis. For example, water based activities such as swimming, showering or even exposure to rain, have traditionally not been recommended due to potential damage to the external part. Further to this, the visual presence of the external part can result in a degree of embarrassment to the wearer, especially for children, where a degree of social stigma may still exist.

It is for these reasons that totally implantable hearing prosthesis systems have been proposed. Such systems provide all components of the prosthesis implanted within the recipient, resulting in a prosthesis that is invisible to the casual onlooker.

However, in order to provide a totally implanted hearing prosthesis system, there is a need to provide an acoustic sensor that can be implanted within the recipient, and which is still capable of detecting speech and ambient sounds with a high degree of precision.

SUMMARY

The present invention is directed towards providing an implantable acoustic sensor which utilises the natural acoustic functions of the outer and middle ear, by detecting the acoustic pressure variations in the naturally present fluid inside the cochlea (perilymph).

In accordance with one aspect of the present invention, there is provided An implantable acoustic sensor for a hearing prosthesis, said sensor including:
    an elongate member operatively adapted to be implanted into a cochlea; and a piezoelectric element being functionally co-operable with said elongate member for detecting pressure waves in the perilymph of the cochlea and producing corresponding electrical signals.

In accordance with another aspect of the present invention, there is provided a hearing prosthesis comprising:
    a piezoelectric sensor having an elongate portion adapted for implantation into a cochlea;
    a signal processor in communication with said sensor; and
    a stimulator for actuating therapy in accordance with said signal processor,
    wherein said sensor operatively senses pressure waves in the perilymph of the cochlear via said elongate portion and sends corresponding electrical signals to said signal processor, said stimulator actuating therapy in response to said electrical signals.

The stimulator may be any form of hearing prosthesis, including a cochlear implant, hearing aid, or any other form of prosthesis. The present invention is not limited to any particular form of stimulation.

Whilst the present invention is valuable in the design of a fully implantable device, it may be applied in other systems where an external component is retained.

BRIEF DESCRIPTION OF THE DRAWINGS

By way of example only, a number preferred embodiments of the invention are now described with reference to the accompanying drawings, in which.

DETAILED DESCRIPTION

Before describing the features of the present invention, it is convenient to briefly describe the overall construction and function of a typical cochlear implant system.

Figure 1:
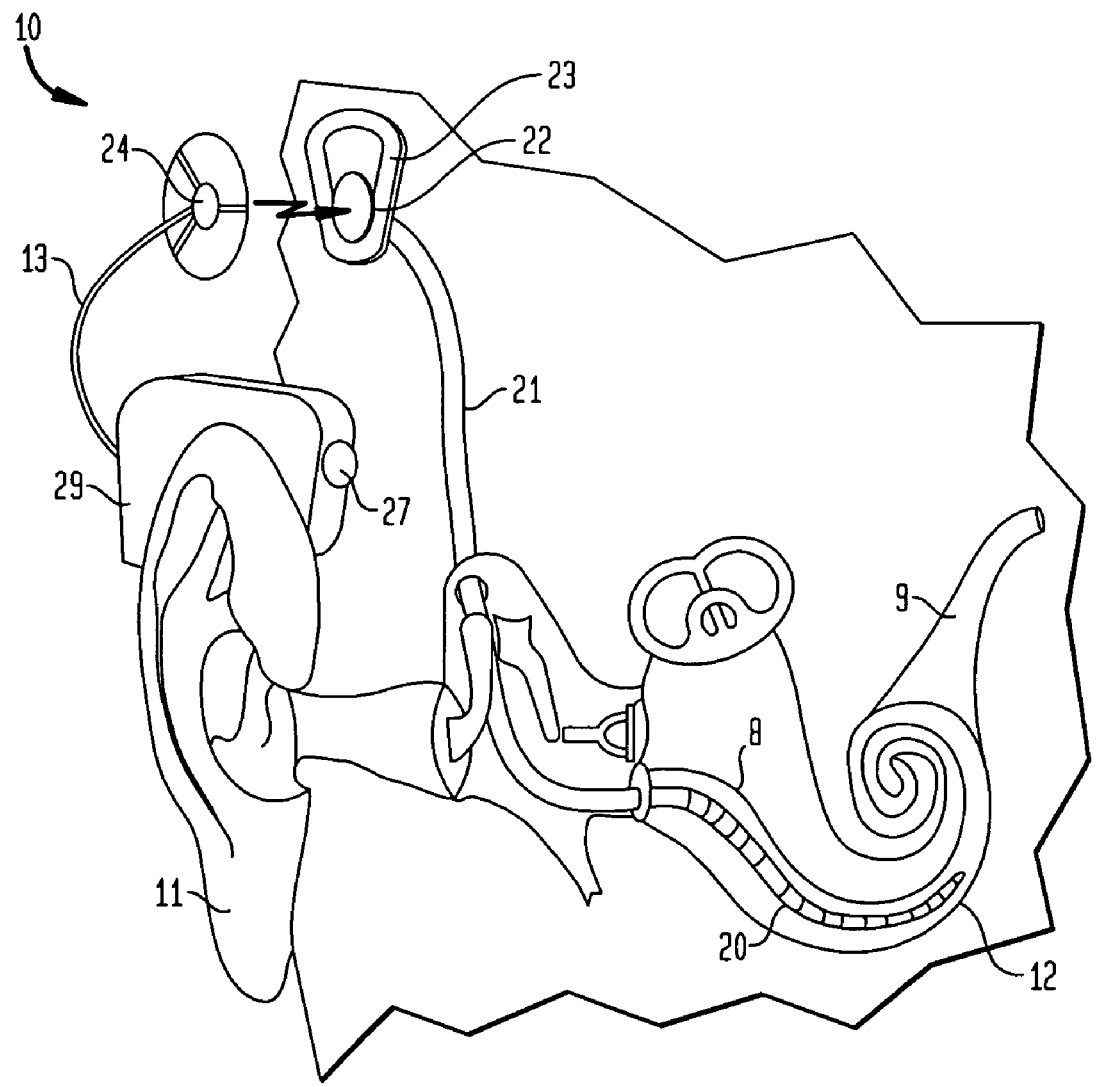
FIG. 1 is a simplified, schematic view of a conventional cochlear implant system.

Referring to FIG. 1, the cochlear implant system 10 includes two main parts, an external part including a speech processor 29, and an internal or implanted part including an implanted receiver and stimulator unit 22.

The external part includes a microphone 27. The speech processor 29 is, in this illustration, constructed and arranged so that it can fit behind the outer ear 11 and is held in place behind the outer ear 11 via an ear-hook arrangement (not shown). Alternative versions may be worn on the body. Attached to the speech processor 29 is a transmitter coil 24 that transmits electrical signals to the implanted unit 22 via a radio frequency (RF) link.

The implanted part includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 and the nerve cells within the cochlea 12 thereby stimulating the auditory nerve 9. The operation of such a device is well understood in the art, and is described, for example, in U.S. Pat. No. 4,532,930.

As can be appreciated from FIG. 1, a conventional cochlear implant system is quite visible and requires a number of external components to capture and process the sound into a coded signal for transmission to the implanted unit 22. Since the sound is captured externally, conventional hearing aid microphones have traditionally been employed to perform such a function.

The natural human auditory system and the natural acoustic functions of the outer and middle ears are the ideal sensing mechanism for providing filtering, directionality and amplification of environmental sound. The human ear essentially picks up air borne sound waves and converts them into fluid borne pressure inside the cochlea. The middle ear acts as an impedance transformer to match the low impedance of the air to the high impedance of the perilymph (i.e. the fluid in the scala vestibuli and scala tympani in the cochlea). As a result, the pressure transfer ratio from the tympanic membrane to the scala vestibuli peaks to be more than 30 dB around 1 kHz and drops to be less than 0 dB below 100 Hz.

Figure 2:
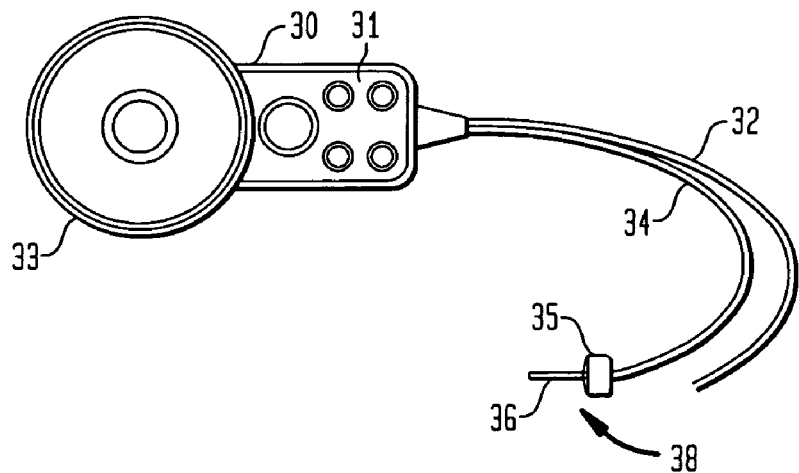
FIG. 2 is a view of totally implantable cochlear implant system employing an implantable acoustic sensor according to a first arrangement.

An example of a cochlear implant package 30 having an implantable sensor according to this disclosure will now be described with reference to FIG. 2. The implant package 30 is conventionally arranged in this example, that is, with an implanted component and an external control unit. Whilst the present invention provides an implantable acoustic sensor, which may be advantageously employed in a totally implanted device, it is not limited in application to such a device. The practical implementation discussed below includes an external component.

The implant package 30 includes a hermetically sealed housing 31, a transmitter/receiver coil 33, an electrode array member 32 and lead 34 having a perilymph acoustic sensor 38.

The housing 31 contains electronic circuitry, including a power source, operatively associated with the implant 30. The transmitter/receiver coil 33 is capable of receiving and/or transmitting data from/to an external control unit, such as a speech processor unit as described in FIG. 1. The transmitter/receiver coil 33 is also capable of communicating with an external power recharging source for recharging the implanted power source.

The electrode array 32 is connected to the housing 31 at its proximal end, and terminates at its distal end with a plurality of electrode elements. The electrode array 32 is positionable within the cochlea to provide electrical stimulation so as to generate a perception of sound, in a manner such as that previously described and as is generally understood in the art.

It will be appreciated that in the implementation shown, the electrical signals representative of the ambient acoustic signals will need to transmitted to the external component for processing, so as to produce the stimulus signals for electrode array 32. Existing cochlear implants include telemetry transmission arrangements which could be utilised for this purpose, with suitable modifications. Any suitable transmission arrangement could be used. In the case of an acoustic hearing aid, a short range RF communications system could be provided. In a totally implanted system, the acoustic signals could be processed within the implant 30.

Figure 3A:
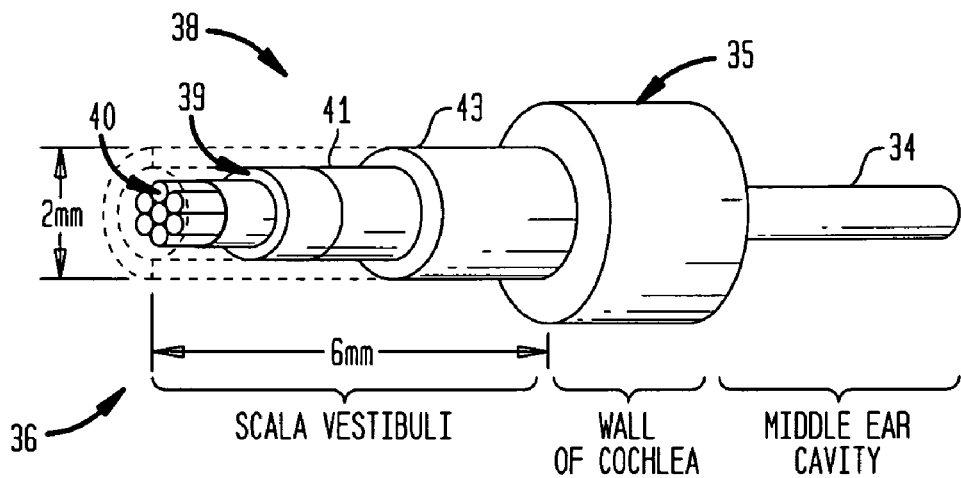
FIG. 3A is a detail view of the implantable acoustic sensor of FIG. 2.

Turning now to FIG. 3A, sensor 38 comprises a collar member 35 and an elongate member 36. The collar member 35 is disposed between the elongate member 36 and the lead 34. The collar member 35 is generally adapted to be fitted external of the cochlea and is operatively in contact with the external wall of the cochlea, to seal perilymph inside the cochlea and to stabilise the sensor 38. Preferably, the collar 35 is made from a biocompatible material such as titanium.

Figure 5:
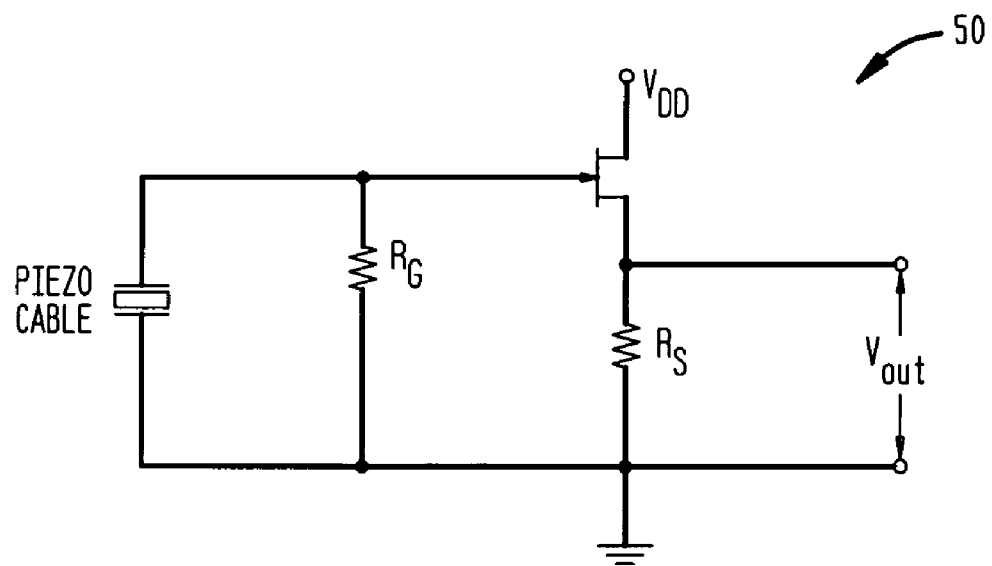
FIG. 5 is a circuit diagram of a JFET source follower.

The collar 35 also provides in this implementation a hermetically sealed cylindrical housing for an interface, or preamplifier circuit 50, as shown for example in FIG. 5 as a JFET trans-impedence amplifier, the operation of which will be further described below.

The elongate member 36 includes a piezoelectric element 39 capable of sensing pressure changes in a surrounding environment and generating an corresponding electrical signal. The scope of 'piezoelectric' within the context of this specification includes piezo polymers and piezoceramics, and any other suitable material exhibiting the piezoelectric effect.

The preamplifier circuit 50 lowers the source impedance of piezoelectric element 39 and minimises noise generated in lead 34. The preamplifier circuit 50 processes the electrical signal received from the elongate member 36, and outputs a signal for further processing as an signal input to the cochlear implant system 10.

The elongate member 36 is surgically inserted into the scala vestibuli so as to be in contact with the perilymph. The elongate member 36 is configured to detect changes in fluid pressure of the perilymph fluid, corresponding to ambient sound signals. These pressure waves are induced by the previously described mechanical functions of the middle ear. The pressure changes induce an electrical signal in the piezoelectric element 39, and the signal is transferred along the elongate member 36 to the collar 35.

Both the electrode array 32 and the elongate member 36 are inserted into the cochlea using similar techniques. Generally, the electrode array 32 is inserted into the scala tympani and the elongate member 36 is inserted into scala vestibuli, resulting in the need to create two separate cochleostomies. It should be appreciated that if the acoustic sensor 38 was employed in an implantable hearing aid application, then only one cochleostomy would be required.

However, the present invention may be applied in alternative surgical procedures, provided that the sensor is appropriately positioned in or in communication with the perilymph.

The elongate member 36 comprises a centre core conductor 40, a piezoelectric layer 39, and a surface electrode 41. The centre core conductor 40 acts as the signal electrode, and the surface electrode 41 acts as the ground electrode and shield. The surface electrode 41 may be any suitable biocompatible conductor, for example Ti or Pt thin film.

A thin-film passivation layer (not shown) is also provided around the surface electrode 41 to provide electrical insulation between the electrode and the surrounding perilymph. Any suitable biocompatible insulator may be used. This passivation layer in this implementation comprises a layer of material such as parylene or silicon rubber.

A piezoelectric material is one in which the imposition of mechanical stress or strain produces an electrical polarisation across the material. The piezoelectric layer 39 comprises a layer of piezoelectric material, so that pressure waves in the periplymph are converted to an electrical signal. The piezoelectric layer 39 can be a synthetic polymer having such properties, known as piezopolymer films or piezo films, such as polyvinylidene fluoride (PVDF) and its copolymers. Such piezo film transducers are small, inexpensive and solid-state, and so are more rugged than typical electrostatic transducers and have a wide frequency bandwidth.

Figure 3B:
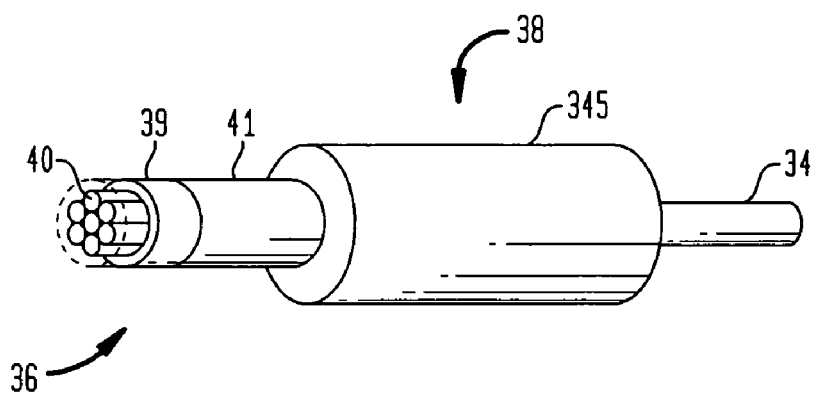
FIG. 3B is a detail view of an alternative implantable acoustic sensor.

FIG. 3B shows another arrangement of the perilymph acoustic sensor 38, in which the collar member 35 has a cylindrical form and is adapted to fit into the opening made in the wall of a cochlea, so as to sealingly secure the sensor 38 in place.

Figure 4A:
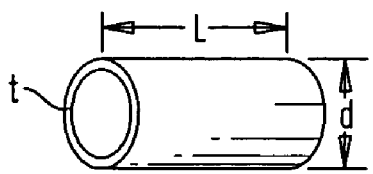
FIGS. 4a and 4b are schematic drawings used to model of a piezoelectric element according to this disclosure.
Figure 4B:
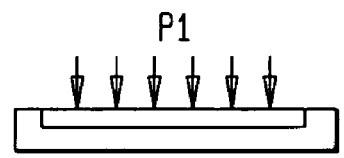

Turning now to FIGS. 4a and 4b, some basic theoretical aspects related to the design of the piezoelectric layer 39 will be described. As is evident in FIG. 3B, the piezoelectric layer 39 has a cylindrical shape with a length L, a wall thickness t, and a mean diameter d which is the average of the outer and inner diameters. In operation, the piezoelectric layer 39 is immersed in fluid within the cochlea, and an acoustic pressure $P_i$ is applied on its outer surface. Therefore, assuming that the centre core conductor 40 is incompressible, the piezoelectric layer 39 can be modelled as a piezopolymer tile sitting on a solid foundation, having a length L, a width of $\pi d$, and a thickness t.

The surface area, S, of the tile is $\pi dL$, so its capacitance is given as:

$$C = \varepsilon \frac{S}{t} = \varepsilon \frac{\pi dL}{t} \quad (1)$$

Under the acoustic pressure $P_i$, the charge Q generated is given as:

$$Q = d_h S P_i = d_h \pi dL P_i \quad (2)$$

where $d_h$, is the piezo coefficient in pC/N.

Thus, the open-circuit voltage $V_o$ is:

$$V_o = \frac{Q}{C} = \frac{d_h \pi dL P_i}{\varepsilon \frac{\pi dL}{t}} = \frac{d_h}{\varepsilon} P_i t = g_h P_i t \quad (3)$$

where $d_h$ is the hydrostatic strain constant in C/N, $g_h$ is the stress constant in $V_m/N$ and $g_h = d_h/e$.

Therefore, the open circuit sensitivity of the sensor model is:

$$\frac{V_o}{P_i} = g_h t \quad (4)$$

Figure 10:
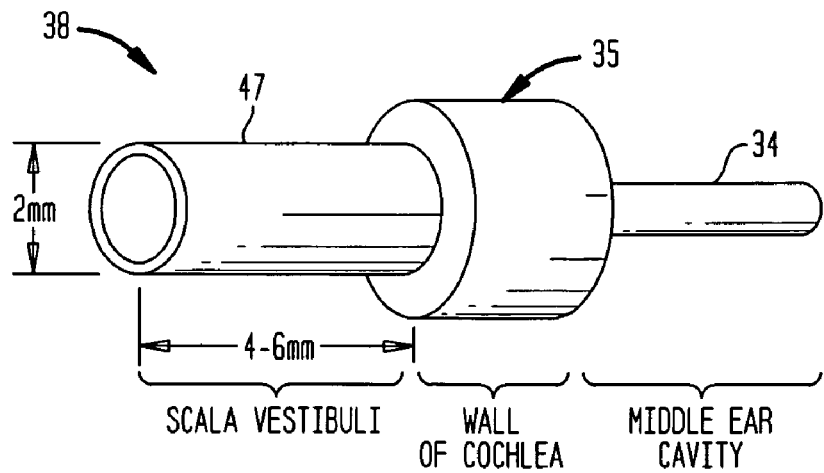
FIG. 10 is a view of yet another arrangement of the implantable acoustic sensor.

With such a design and the ability to alter the layer parameters such as the wall thickness t and the diameter d, it is therefore possible to provide a sensor having suitable properties to act effectively as a microphone device when implanted so as to communicate with the perilymph. It will be appreciated that the appropriate dimensions can be determined by those skilled in the art by reference to the properties of the materials selected. Illustrative dimensions are shown in FIGS. 3A and 10.

As previously discussed, in use, the elongate member 36 is implanted into the scala vestibuli where it is subject to pressure variations in the perilymph, representative of environmental sounds sensed and processed by the natural acoustic system. The pressure variations are detected by the piezoelectric layer 39 in the manner described above, and the resulting change in the electric field of the piezoelectric layer 39 is then carried by the centre core conductor 40 to the collar 35. The collar 35 houses a preamplifier to condition and treat the signal received from the piezoelectric layer 39 for processing by the implant 30. FIG. 5 shows one such amplifier suitable for this purpose, namely a JFET preamplifier.

As the piezoelectric layer 39 has a very low capacitance of a few pF, it is important to minimise the stray capacitance between the sensor element and the JFET preamplifier. In this regard, in the present implementation, surface mounted resistors are directly mounted to the pins of the JFET inside the collar 35. By selecting the appropriate resistance of the surface mounted resistors, the gain of the preamplifier can be adjusted accordingly, as will be understood by those skilled in the art.

Following preamplification, the treated signal is transmitted to the implant package 30 via the electric cable 34, where the signal can be used as a microphone input, representative of ambient sound or speech.

Figure 6:
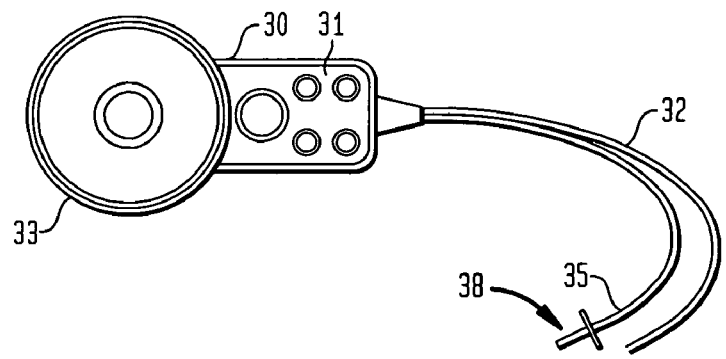
FIG. 6 is a view of a totally implantable cochlear implant system employing an implantable acoustic sensor.

Whilst the above arrangement uses a preamplifier in the collar 35 to treat the signal prior to the signal being received by the implant package 30, it is also envisaged that the preamplification circuit could be provided within the implant housing 31. Such an arrangement is shown in FIG. 6. Unlike the arrangement described in relation to FIG. 2, there is no requirement for an additional hermetic package to house a remote preamplifier. Rather, the amplification circuit is provided in the implant housing 31, which directly receives the signal from the perilymph acoustic sensor 38 via the lead 34. Such an arrangement allows a more flexible design of the perilymph acoustic sensor 38 without the need to include a hermetic package to house the preamplifier. However, it creates a longer path for the unamplified signal to pass along lead 34 prior to pre-amplification.

Figure 7:
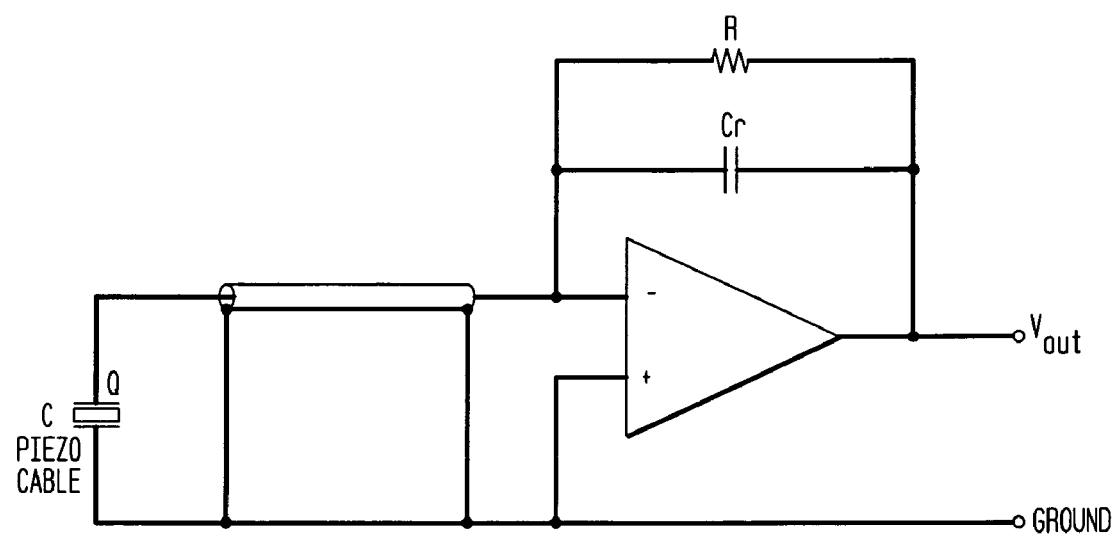
FIG. 7 is a circuit diagram of a charge amplifier circuit.

FIG. 7 shows an example of one type of amplification circuit which may be provided in the implant package of FIG. 6, where:

C represents the source capacitance of the piezoelectric layer 39,

Q represents the electric charge present on the centre core electrode, $C_f$ represents the feedback capacitance, and $V_{out}$ is the output voltage and is determined by $V_{out} = Q/C_f$, which is independent of the source capacitance of the piezoelectric layer 39.

The system of FIGS. 6 and 7 is simplified by placing the charge amplifier inside the implant package and linking it to sensor 38 via a shielded cable 34.

Figure 8:
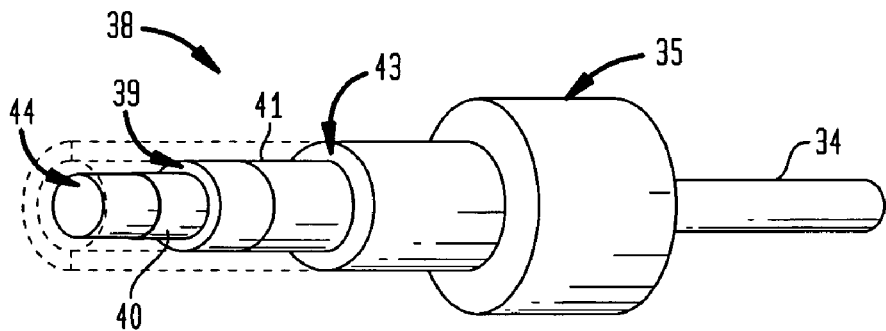
FIG. 8 is a view of yet another arrangement of an implantable acoustic sensor.
Figure 9:
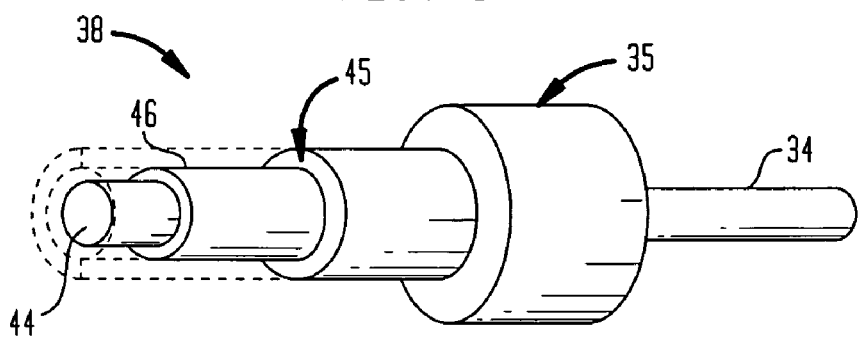
FIG. 9 is a view of yet another arrangement of the implantable acoustic sensor.

FIGS. 8 to 10 show alternative arrangements of the perilymph acoustic sensor 38, where the preamplifier is housed within the hermetic package 35. All of the sensor designs could be used with either a preamplifier in the package 35, or with direct connection to an preamplifier in the implant package 31.

FIG. 8 is similar to FIG. 3A in that a centre core conductor 40 is shown with the piezoelectric layer 39 and the surface/ground electrode 41. In this example, the centre core conductor is formed as a conductive layer 40 around an insulating core 44, for example of Silastic or similar silicone rubber. The piezoelectric layer 39 is a PVDF copolymer layer. A layer of flexible coating 43 is placed over the surface/ground electrode 40. The flexible coating is preferably made from a Silastic or parylene thereby forming a passivation layer about the surface electrode 41, and providing electrical insulation to the perilymph.

FIG. 9 shows yet another embodiment of the perilymph acoustic sensor element, similar to that of FIG. 9. However in this arrangement, the piezoelectric layer 39, instead of being constructed from PVDF copolymer, is constructed from a VF2 piezofilm tape with a spiral wrap.

FIG. 10 shows another arrangement for the sensor. Instead of the sensor being inserted into the scala vestibuli, in this arrangement, it is intended that tube 47 acts as a pressure conduit to a sensor located in the collar 35. As can be seen more clearly in the view of FIG. 11, the sensor is located with the housing 35. The acoustic sensor 38 in this case is a piezoceramic hydrophone, rather than the piezo cable sensor as described in relation to FIGS. 2 to 9. Tube 47 is made from a biocompatible material such as titanium and extends into the scala vestibuli, and acts as a pressure inlet to conduct the perilymph to the piezoceramic sensing elements of the hydrophone, situated within the collar 35. As the perilymph is a liquid, it conducts the acoustic signals throughout its volume and so the pressure waves can be detected by the hydrophone outside the cochlear via the tube 47.

Figure 11:
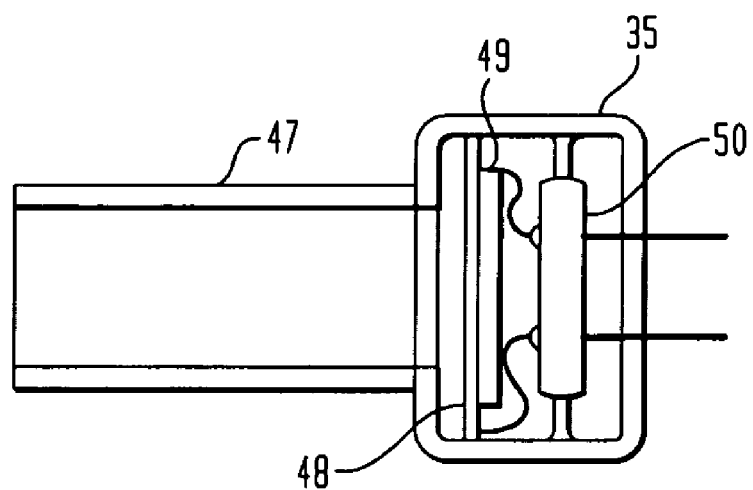
FIG. 11 is a view of one embodiment of the hydrophone arrangement of FIG. 10.

Referring to FIG. 11, the hydrophone consists of a diaphragm 48 made from a suitable material such as titanium, and a piezoceramic disc 49, bonded so as to form a piezo unimorph. A unimorph is made by bonding a thin layer of piezo material to a non-piezo material. In this case the pressure incident on the diaphragm is transmitted to the piezoceramic disc to produce the required electrical signal. The unimorph is hermetically sealed within the collar 35, with a ceramic feedthrough device 50 providing an electrical signal path from the unimorph to the implant.

Figure 12:
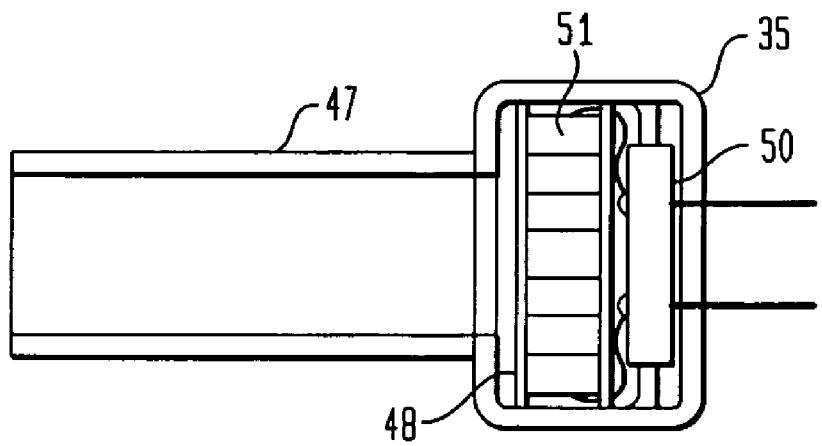
FIG. 12 is a view of another embodiment of the hydrophone arrangement of FIG. 11.

FIG. 12 shows an alternative arrangement to that shown in FIG. 11. The piezo unimorph arrangement is replaced with a plurality of piezoceramic elements (for example cubes or rings) positioned between a pair of titanium diaphragms 48. Such an arrangement increases the volume of the piezoceramic and hence the sensitivity of the system to changes in fluid pressure of the perilymph.

In each of the above hydrophone arrangements, the perilymph acoustic sensor 38 is positioned such that the elongate tubing 47 is in fluid communication with the perilymph to thereby detect changes and variations in the fluid pressure.

For all of the implementations, it is important that following surgical insertion of the elongate member 36 and/or the tubing 47 into the cochlea, the opening is sealed to ensure that the hydrodynamic nature of the cochlea is maintained. The collar 35 of the perilymph acoustic sensor 38 assists in performing this function as it is designed to be incorporated into the wall of the cochlea, and is of a larger dimension than the elongate member 36 and the tubing 47. The sealing arrangement can be further facilitated by incorporating a hydroxylapatite coating on the collar 35, which promotes integration with the bone structure to facilitate sealing. It is also envisaged that a silicone rubber flange could also be placed around the elongate member 36 and/or tubing 47 to function both as a sealing plug and a stop for surgical insertion.

The implantable acoustic sensor according to this disclosure can utilise the natural acoustic functions of the outer and middle ear, by detecting the acoustic pressure of the perilymph within the cochlea. The implantable acoustic sensor can be used in conjunction with an implantable hearing prosthesis to overcome the need for an external microphone in such systems.

Further, the implantable acoustic sensor can function as part of a system having other types of acoustic sensors. For example, the system described in W0 02/05590 includes one or more subcutaneous microphones that function as part of a totally implantable cochlear implant system. In this alternative arrangement, the implantable acoustic sensor according to this disclosure is configured to operate in parallel with, or as an alternative to those subcutaneous microphone(s), thereby enabling a choice of multiple types of acoustic inputs to be provided for a totally implantable cochlear implant system. This arrangement can improve the overall performance of the totally implantable cochlear implant system by providing a supplementary means of capturing sound, rather than having to rely on the performance of the particular subcutaneous microphone(s) used. The multiple sensor system can also facilitate the selective use of different types of sensors in various environmental conditions, where the users or the controlling software may select different settings for sensitivity, directivity and the like.

The implantable acoustic sensor according to this disclosure requires no moving parts or air gaps, which are highly desirable attributes in implant design. The elimination of complex fixation and alignment steps reduces the chances of complication and device failure.

It will be appreciated that the present invention operates on the assumption that the perilymph is receiving acoustic signals corresponding to ambient sound. Accordingly, if the mechanical structures of the middle and outer ear are compromised so that there is no or inadequate mechanical transmission, then sensing acoustic signals in the perilymph will not be effective.

It will be appreciated by persons skilled in the art that numerous variations and/or modifications may be made to the invention as shown in the specific examples without departing from the scope of the invention as broadly described.

What is claimed is:

1. An implantable acoustic sensor for a hearing prosthesis, said sensor including:
   an elongate member operatively adapted to be implanted into a cochlea;
   a piezoelectric element configured to be functionally cooperable with said elongate member, to detect pressure waves in the perilymph of the cochlea, and to produce corresponding electrical signals; and
   a collar member arranged proximate to one end of said elongate member, wherein said collar member houses a preamplifier circuit configured to process said electrical signals received from said piezoelectric element and to output a preamplified signal.

2. The sensor of claim 1, further comprising:
   a lead configured to electrically connect said collar to the implantable hearing prosthesis, wherein said collar is configured to transmit said processed signals to the implantable hearing prosthesis via said lead.

3. The sensor of claim 1,
   wherein said elongate member is configured to be implanted into the scala vestibuli of the cochlea; and
   wherein said piezoelectric element is configured to detect pressure waves in the perilymph of the scala vestibuli.

4. The sensor of claim 3, wherein said piezoelectric element is a piezoceramic hydrophone.

5. The sensor according to claim 1, wherein said collar member is constructed and arranged to assist in sealing an opening in a wall of the cochlea.

6. The sensor of claim 5, wherein said collar is adapted to contact an external wall of the cochlea to seal the cochlea and stabilize said sensor.

7. The sensor of claim 6, wherein said collar has a diameter which is greater than a diameter of said elongate member.

8. The sensor of claim 5, wherein said collar houses a preamplifier circuit which processes said electrical signal received from said piezoelectric element and outputs a processed signal for further processing by an implantable hearing prosthesis.

9. The sensor of claim 8, wherein said collar is provided with an electric cable to transmit said processed signal for further processing by said implantable hearing prosthesis.

10. The sensor of claim 1, wherein said piezoelectric element extends substantially along the length of said elongate member.

11. The sensor of claim 10, wherein said piezoelectric element forms a layer around said elongate member.

12. The sensor of claim 1, wherein said piezoelectric element is a piezo cable sensor.

13. The sensor of claim 1, wherein said piezoelectric element is a polymer.

14. The sensor of claim 13, wherein said piezoelectric element is a polyvinylidene fluoride (PVDF) or PVDF copolymer film taped on the surface of, and spirally wound around said elongate member.

15. The sensor of claim 1, wherein said elongate member comprises:
a core conductor, and wherein said piezoelectric element forms a layer about said core conductor.

16. The sensor of claim 15, wherein said core conductor is configured to perform the function of a signal electrode.

17. The sensor of claim 15, wherein a signal electrode is disposed around said piezoelectric element layer and said core conductor.

18. The sensor of claim 15, wherein said signal electrode acts as a ground electrode and shield.

19. The sensor of claim 18, wherein a thin film passivation layer is provided over said signal electrode to provide electrical insulation between said signal electrode and the perilymph.

20. The sensor of claim 19, wherein said passivation layer is parylene or silicon rubber.

21. A cochlear implant, comprising:
an electrode array;
an implantable acoustic sensor, comprising:
an elongated member configured to be implanted onto a cochlea wherein said elongate member includes a core conductor;
a piezoelectric element forming a layer about said core conductor configured to detect pressure waves in the perilymph of the cochlea when said elongate member is implanted in the cochlea, and to produce electrical signals corresponding to said detected pressure waves.

22. The cochlear implant of claim 21, wherein said sensor further comprises:
a collar member arranged proximate to one end of said elongate member, said collar member being operatively adapted to assist in sealing an opening in a wall of the cochlea.

23. The cochlear implant of claim 22, wherein said collar is adapted to contact an external wall of the cochlea to seal the cochlea and stabilize said sensor.

24. The cochlear implant of claim 23, wherein said collar has a diameter which is greater than a diameter of said elongate member.

25. The cochlear implant of claim 22, wherein said collar houses a preamplifier circuit which processes said electrical signal received from said piezoelectric element and outputs a processed signal for further processing by the cochlear implant.

26. The cochlear implant of claim 25, wherein said collar is provided with an electric cable to transmit the processed signal for further processing by the cochlear implant.

27. The cochlear implant of claim 21, wherein said piezoelectric element forms a layer around said elongate member.

28. The cochlear implant of claim 21, wherein said piezoelectric element is a polymer.

29. The cochlear implant of claim 28, wherein said piezoelectric element is a polyvinylidene fluoride (PVDF) or PVDF copolymer film.

30. The cochlear implant of claim 21, wherein said core conductor acts as a signal electrode.

31. The cochlear implant of claim 21, wherein a signal electrode is disposed around said piezoelectric element layer and said core conductor.

32. The cochlear implant of claim 31, wherein said signal electrode acts as a ground electrode and shield.

33. The cochlear implant claim 32, wherein a thin film passivation layer is provided over said signal electrode to provide electrical insulation between said signal electrode and the perilymph.

34. The cochlear implant of claim 33, wherein said passivation layer is parylene or silicon rubber.

35. An implantable acoustic sensor for a hearing prosthesis, comprising:
an elongate member configured to be implanted into a cochlea, wherein said elongate member includes a core conductor; and
a piezoelectric element that forms a layer about said core conductor, wherein said piezoelectric element is configured to detect pressure waves in the perilymph of the cochlea when said elongate member is implanted in the cochlea and to produce electrical signals corresponding to said detected pressure waves.

36. The sensor of claim 35, further comprising:
a collar member arranged proximate to one end of said elongate member, said collar member being operatively adapted to assist in sealing an opening in a wall of the cochlea.

37. The sensor of claim 36, wherein said collar houses a preamplifier circuit which processes said electrical signal received from said piezoelectric element and outputs a processed signal for further processing by said hearing prosthesis.

38. The sensor of claim 37, wherein said collar is provided with an electric cable to transmit the processed signal for further processing by said hearing prosthesis.

39. The sensor of claim 35, wherein said piezoelectric element extends substantially along the length of said core conductor.

40. The sensor of claim 35, wherein said piezoelectric element is a polymer.

41. The sensor of claim 40, wherein said piezoelectric element is a polyvinylidene fluoride (PVDF) or PVDF copolymer film.

42. The sensor of claim 41, wherein said core conductor acts as a signal electrode.

43. The sensor of claim 36, wherein said collar is adapted to contact an external wall of the cochlea to seal the cochlea and stabilize the sensor.

44. The sensor of claim 43, wherein said collar has a diameter which is greater than a diameter of said elongate member.

45. The sensor of claim 41, wherein a signal electrode is disposed around said piezoelectric element layer and said core conductor.

46. The sensor of claim 45, wherein said signal electrode acts as a ground electrode and shield.

47. The sensor claim 46, wherein a thin film passivation layer is provided over said signal electrode to provide electrical insulation between said signal electrode and the perilymph.

48. The sensor of claim 47, wherein said passivation layer is parylene or silicon rubber.

49. A method for detecting acoustic waves in the perilymph of a cochlea, comprising:
   implanting an elongate member into the cochlea, said elongate member comprising a piezoelectric element extending substantially along the length of said elongate member;
   detecting pressure waves in the perilymph with said piezoelectric element; and
   generating electrical signals corresponding to the detected pressure waves.

50. The method according to claim 49, further comprising:
   processing the electrical signal generated by said piezoelectric element; and
   outputting a processed signal for further processing by said hearing prosthesis.

51. A method for detecting acoustic waves in the perilymph of a cochlea, comprising:
   implanting an elongate member into the cochlea, said elongate member comprising a core conductor and a piezoelectric element that forms a layer about said core conductor;
   detecting pressure waves in the perilymph with said piezoelectric element; and
   generating electrical signals corresponding to the detected pressure waves.

52. The method according to claim 51, further comprising:
   processing the electrical signal generated by said piezoelectric element; and
   outputting a processed signal for further processing by said hearing prosthesis.

\* \* \* \* \*